(12) United States Patent
Chang et al.

(10) Patent No.: US 11,051,742 B2
(45) Date of Patent: Jul. 6, 2021

(54) WEARABLE DEVICE AND RESPIRATION SENSING MODULE

(71) Applicant: Industrial Technology Research Institute, Hsinchu (TW)

(72) Inventors: Yi-Ming Chang, Hsinchu (TW); Chih-Wei Chen, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 507 days.

(21) Appl. No.: 15/838,368

(22) Filed: Dec. 12, 2017

(65) Prior Publication Data

US 2019/0133479 A1 May 9, 2019

(30) Foreign Application Priority Data

Nov. 7, 2017 (TW) .................................. 106138397

(51) Int. Cl.
*A61B 5/08* (2006.01)
*A61B 5/322* (2021.01)
(Continued)

(52) U.S. Cl.
CPC ............ *A61B 5/322* (2021.01); *A61B 5/0816* (2013.01); *A61B 5/113* (2013.01); *A61B 5/25* (2021.01);
(Continued)

(58) Field of Classification Search
CPC combination set(s) only.
See application file for complete search history.

(56) References Cited

U.S. PATENT DOCUMENTS 4,308,870 A * 1/1982 Arkans ................ A61B 5/1135
338/38
9,704,209 B2 7/2017 Proud et al.
(Continued)

FOREIGN PATENT DOCUMENTS

CN 101632585 1/2010
CN 106894133 6/2017
(Continued)

OTHER PUBLICATIONS

Chaoyi Yan et al., "Stretchable and Wearable Electrochromic Devices", ACS NANO, Dec. 21, 2013, pp. 316-322.
(Continued)

*Primary Examiner* — Eric J Messersmith
(74) *Attorney, Agent, or Firm* — JCIPRNET

(57) ABSTRACT

A wearable device and respiration sensing module are provided. The wearable device includes a first respiration sensing module and a second respiration sensing module. The first respiration sensing module is configured to sensing respiration of a user to obtain a first respiration information. The second respiration sensing module is configured to sensing respiration of the user to obtain a second respiration information. The second respiration sensing module includes a substrate, a first electrode, a second electrode and a stretchable conductive element. The first electrode and the second electrode are disposed on a first surface of the substrate. The stretchable conductive element is physically and electrically connected between the first electrode and the second electrode. The respiration of the user is judged according to the first respiration information and the second respiration information.

22 Claims, 6 Drawing Sheets

(51) Int. Cl.
*A61B 5/113* (2006.01)
*A61B 5/25* (2021.01)
*A61B 5/00* (2006.01)
*A61B 5/0205* (2006.01)
*A61B 5/339* (2021.01)

(52) U.S. Cl.
CPC ........... *A61B 5/0006* (2013.01); *A61B 5/0205* (2013.01); *A61B 5/339* (2021.01); *A61B 5/6801* (2013.01); *A61B 2562/0261* (2013.01)

(56) References Cited

U.S. PATENT DOCUMENTS

2017/0176167 A1  6/2017  Keller et al.
2018/0249767 A1* 9/2018  Begriche ............. H05K 1/0283

FOREIGN PATENT DOCUMENTS

| | | |
|---|---|---|
| CN | 206261599 | 6/2017 |
| NO | 2017075703 | 5/2017 |
| TW | I483707 | 5/2015 |
| TW | 201635932 | 10/2016 |

OTHER PUBLICATIONS

Morteza Amjadi et al., "Highly Stretchable and Sensitive Strain Sensor Based on Silver NanowireElastomer Nanocomposite", ACS NANO, Apr. 21, 2014, pp. 5154-5163.
Philippe Guay et al., "Wearable Contactless Respiration Sensor Based on Multi-Material Fibers Integrated into Textile", Sensors, May 6, 2017, pp. 1-13.
"Office Action of Taiwan Counterpart Application," dated Aug. 23, 2018, pp. 1-8.
"Office Action of China Counterpart Application", dated Mar. 2, 2021, pp. 1-10.

* cited by examiner

WEARABLE DEVICE AND RESPIRATION SENSING MODULE

CROSS-REFERENCE TO RELATED APPLICATION

This application claims the priority benefit of Taiwan application serial no. 106138397, filed on Nov. 7, 2017. The entirety of the above-mentioned patent application is hereby incorporated by reference herein and made a part of this specification.

BACKGROUND

Technical Field

The disclosure relates to a wearable device and respiration sensing module.

Description of Related Art

A respiration pattern is an important indicator for judging vital signs. The mere use of heartbeat as an indicator to judge vital signs may be inadequate. For example, when a baby chokes on milk, the respiration may stop or produce disorders. However, at this point, the heartbeat of the baby may not stop immediately and may only produce a rapid heartbeat situation, which is unable to immediately determine a life-threatening possibility. Therefore, respiration sensing has its importance. The commonly seen respiration sensing devices have acoustic modes, gas flow rate modes and so on, and also have a mode which uses ECG derived respiration (EDR). However, these respiration sensing devices are usually bulky equipment or need to rely on complex calculus, computing system, and there are still concerns on its accuracy.

SUMMARY

The wearable device of an embodiment of the disclosure includes a first respiration sensing module and a second respiration sensing module. The first respiration sensing module is configured to sensing respiration of a user to obtain a first respiration information. The second respiration sensing module is configured to sensing respiration of the user to obtain a second respiration information. The second respiration sensing module includes a substrate, a first electrode, a second electrode and a stretchable conductive element. The first electrode and the second electrode are disposed on a first surface of the substrate. The stretchable conductive element is physically and electrically connected between the first electrode and the second electrode. The respiration of the user is judged according to the first respiration information and the second respiration information.

The respiration sensing module of an embodiment of the disclosure includes a substrate, a first electrode, a second electrode, a stretchable conductive element and a distance control member. The first electrode and the second electrode are disposed on a first surface of the substrate. The stretchable conductive element is physically and electrically connected between the first electrode and the second electrode. The distance control member is configured to control the length of the stretchable conductive element to be greater than or equal to a preset value.

To make the aforementioned disclosure more comprehensible, several embodiments accompanied with drawings are described in detail as follows.

DESCRIPTION OF THE EMBODIMENTS

Figure 1:
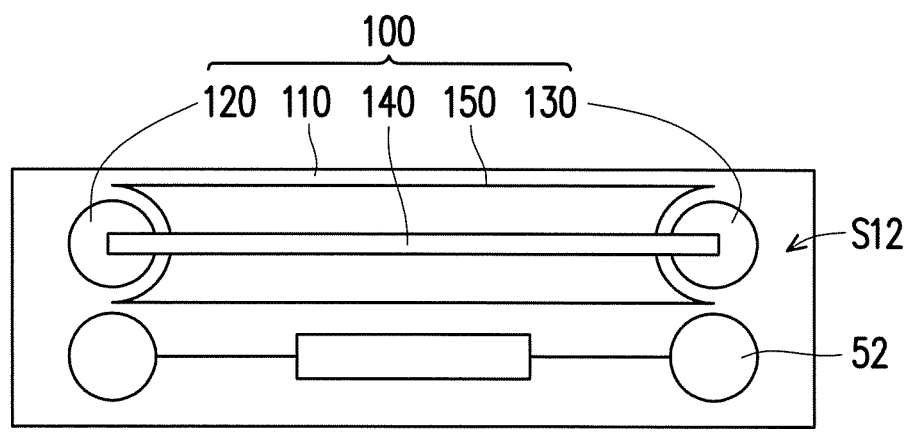
FIG. 1 is a top view schematic diagram of wearable device according to an embodiment of the disclosure.

FIG. 1 is a top view schematic diagram of a wearable device according to an embodiment of the disclosure. Referring to FIG. 1, a wearable device 50 of the embodiment includes a first respiration sensing module 52 and a second respiration sensing module 100. The first respiration sensing module 52 is configured to sensing respiration of a user in a time period to obtain a first respiration information; The second respiration sensing module 100 is configured to sensing respiration of the same user in the same time period to obtain a second respiration information. The second respiration sensing module 100 includes a substrate 110, a first electrode 120, a second electrode 130 and a stretchable conductive element 140. The first electrode 120 and the second electrode 130 are disposed on a first surface S12 of the substrate 110. A stretchable conductive element 140 is physically and electrically connected between the first electrode 120 and the second electrode 130. As the stretchable conductive element 140 is physically connected between the first electrode 120 and the second electrode 130, when the relative distance between the first electrode 120 and the second electrode 130 changes, the length of the stretchable conductive element 140 will also change accordingly. The physical connection between the stretchable conductive element 140 and the first electrode 120 can be connected directly or connected through other objects, and the physical connection between the stretchable conductive element 140 and the second electrode 130 can also be connected directly or connected through other objects. The electrical connection between the stretchable conductive element 140 and the first electrode 120 can be connected directly or connected through other objects, and the electrical connection between the stretchable conductive element 140 and the second electrode 130 can also be connected directly or connected through other objects Since the first respiration sensing module 52 will provide the first respiration information and the second respiration sensing module 100 can provide the second respiration information, the respiration condition of the user can be judged according to the first respiration information and the second respiration information, so as to reduce the possibility of misjudgment. Moreover, according to the law of resistance, that is, R=ρL/A, when the length L of the stretchable conductive element 140 changes, the resistance R also changes accordingly, wherein, A is a cross-sectional area of the stretchable conductive element 140, and ρ is the resistivity of the stretchable conductive element 140. Therefore, when using the wearable device 50, as long as the first electrode 120 and the second electrode 130 of the second respiration sensing module 100 are respectively fixed on the left chest and right chest of the user, the length of the stretchable conductive element 140 will change as the distance between the first electrode 120 and the second electrode 130 caused by the respiration of the user changes. By measuring the resistance change of the stretchable conductive element 140, the length change of the stretchable conductive element 140 can be obtained, so as to obtain the respiration condition of the user.

Figure 2:
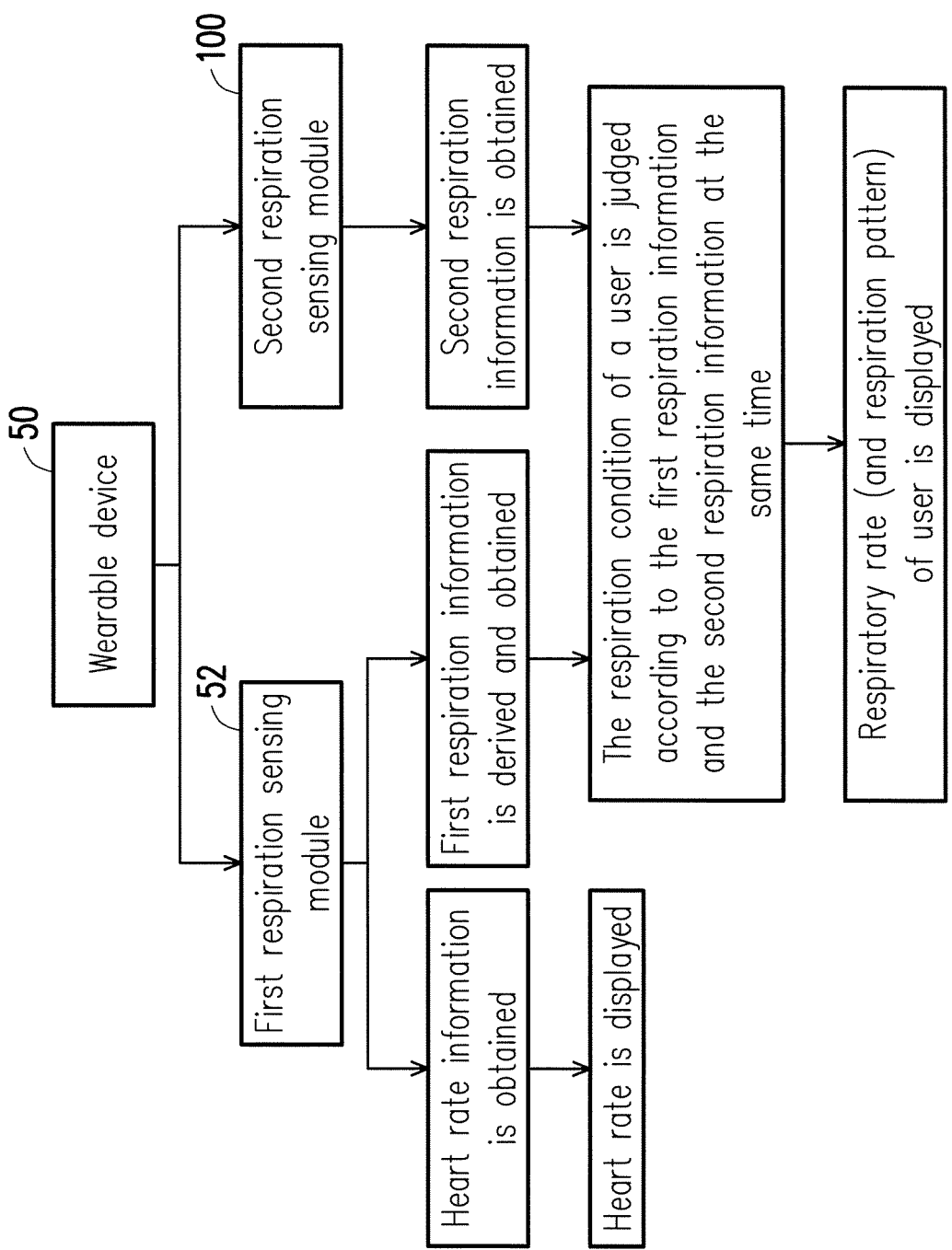
FIG. 2 is a schematic diagram of an operation mode of the wearable device of FIG. 1.

Referring to FIG. 1 and FIG. 2, FIG. 2 is a schematic diagram of an embodiment of an operation mode of the wearable device 50 of FIG. 1, but the wearable device 50 of FIG. 1 is not limited to the implementation of the operation mode shown in FIG. 2. The first respiration sensing module 52 of the embodiment of the disclosure is, for example, an electrocardiogram (ECG) sensing module, a gravity sensing module, an EDR sensing module or other respiration sensing module. When the first respiration sensing module 52 is an EDR sensing module, the heart rate information of the user can be obtained and the heart rate displayed (for example, displayed on a monitor), the first respiration information of the user can also be derived and obtained from the heart rate information. The heart rate information of the user may be displayed through a monitor so that a caregiver can grasp the condition of the user. In addition, the second respiration sensing module 100 may provide the second respiration information. At least one of the first respiration information and the second respiration information includes a respiratory rate or other information. As long as both the first respiration information and the second respiration information are referenced at the same time, the respiration condition of the user can be judged on whether it is, for example, shortness of breath, slow breathing, near death breathing, shallow breathing, cessation of breathing, tidal breathing, deep breathing, air entrapment, long breathing, rapid and deep breathing, sighing and so on. Moreover, since there are two respiration sensing modules, even if any one of the respiratory sensing modules fails, the respiration information provided by the other respiration sensing module can be used to judge the respiration condition of the user. After judging the respiration condition of the user, the respiratory rate, respiration pattern, and/or other respiration parameters of the user may be displayed through the monitor and may be displayed in the mode of a waveform (for example, represented as a waveform with the horizontal axis as time and the vertical axis as amplitude).

Figure 3:
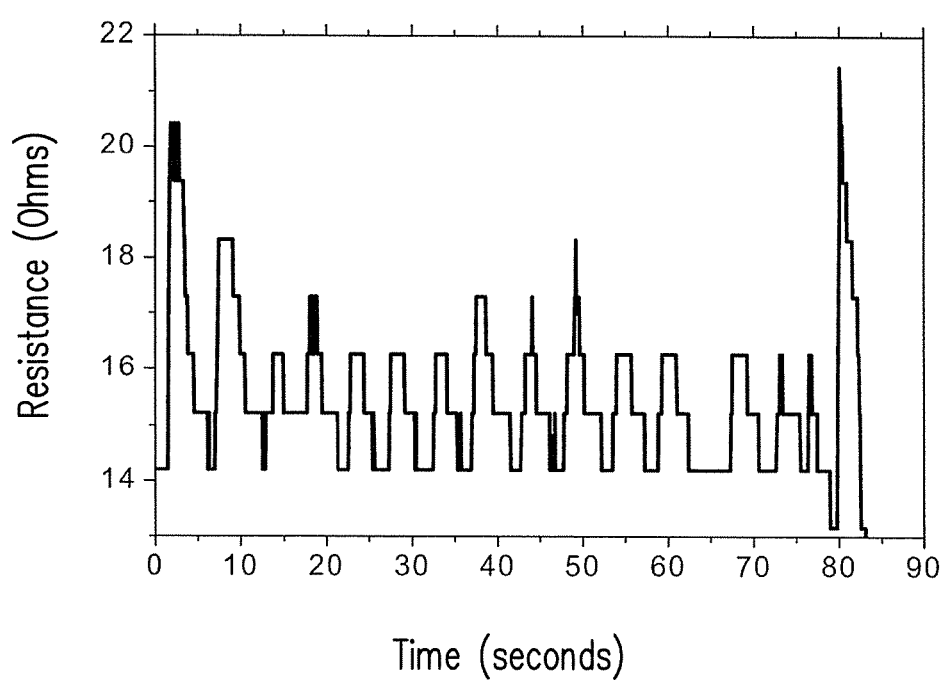
FIG. 3 is a schematic diagram of the respiration information measured by a second respiration sensing module of the wearable device of FIG. 1.

FIG. 3 is a schematic diagram of the respiration information measured by the second respiration sensing module of the wearable device of FIG. 1, wherein the horizontal axis is time, with the unit in seconds, and the vertical axis is resistance, with the unit in ohms. Referring to FIG. 1 and FIG. 3, it can be seen from FIG. 3 that the resistance of the stretchable conductive element 140 changes with the respiration condition of the user. Therefore, the change in waveform of the resistance can correspond to the respiration pattern of the user. In FIG. 3, the resistance value of between 0 seconds to 78 seconds, all in the range of 14 ohms or more, changes with the respiration condition of the user, and when the wearable device 50 is removed from the body of the user at 78th seconds, there is a sharp change of the resistance value that the resistance value returning to zero. In order to reduce possible noise interferences, the length of the stretchable conductive element 140 can be controlled to be greater than or equal to a preset value, such that the measured resistance value of the stretchable conductive element 140 changes above a certain value.

Figure 4:
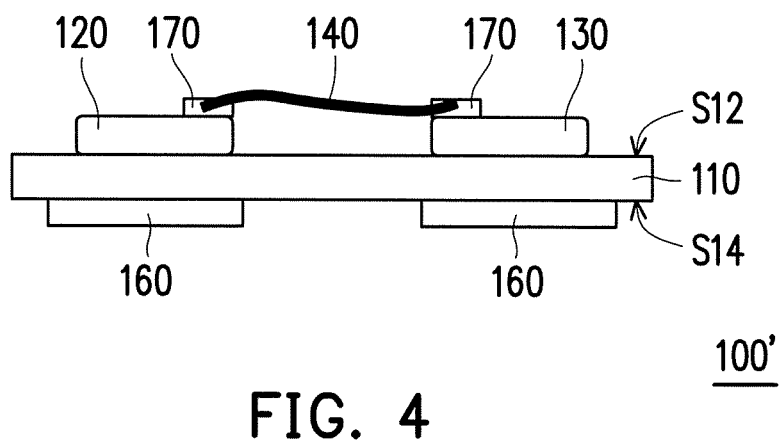
FIG. 4 is a side view schematic diagram of the second respiration sensing module section of the wearable device of FIG. 1.

FIG. 4 is a side view schematic diagram of the second respiration sensing module section of the wearable device of FIG. 1. Referring to FIG. 1 and FIG. 4, the respiration sensing module 100' of FIG. 4 is similar to the second respiration sensing module 100 of FIG. 1, including the substrate 110, the first electrode 120, the second electrode 130, the stretchable conductive element 140 and a distance control member 150, wherein the distance control member 150 is only shown in FIG. 1, and is omitted in FIG. 4. The substrate 100 of the second respiration sensing module 100 of FIG. 1 is, for example, shared with the first respiration sensing module 52. The distance control member 150 is configured to control the length of the stretchable conductive element 140 to be greater than or equal to a preset value. The size of the distance control member 150 remains substantially fixed, thus, the length of the stretchable conductive element 140 can be controlled. In an embodiment of the disclosure, the distance control member 150 is a blocking wall used to limit the distance between the first electrode 120 and the second electrode 130 from being excessively shortened, so as to control the length of the stretchable conductive element 140 to be greater than or equal to the preset value. The structures of the respiration sensing module 100' of FIG. 4 and the second respiration sensing module 100 of FIG. 1 are simple, do not require additional amplifying circuit, and the cost is lower.

In addition, the substrate 110 of the embodiment of the disclosure, for example, is a stretchable substrate so that the distance between the first electrode 120 and the second electrode 130 disposed on the substrate 110 may change with the respiration of the user. The material of the substrate 110 includes material having tensile properties such as plastic, rubber, silicone, or other suitable materials. In addition, the respiration sensing module 100' of the embodiment of FIG. 4 further includes a plurality of patches 160, disposed on a second surface S14 of the substrate 110 opposite to the first surface S12, and positioned correspondingly to the first electrode 120 and the second electrode 130. The patches 160 are configured to fix the first electrode 120 and the second electrode 130 respectively onto the body of the user, and drive the first electrode 120 and the second electrode 130 to move with the respiration of the user. The material of the patches 160 includes a sticky material for attachment to a body surface or other suitable material. The material of at least one of the first electrode 120 and the second electrode 130 includes metal, conductive polymer or other suitable conductive material, or other suitable material. For example, both ends of the stretchable conductive element 140 may be physically and electrically connected to the first electrode 120 and the second electrode 130 by the silver paste 170 respectively.

Figure 5:
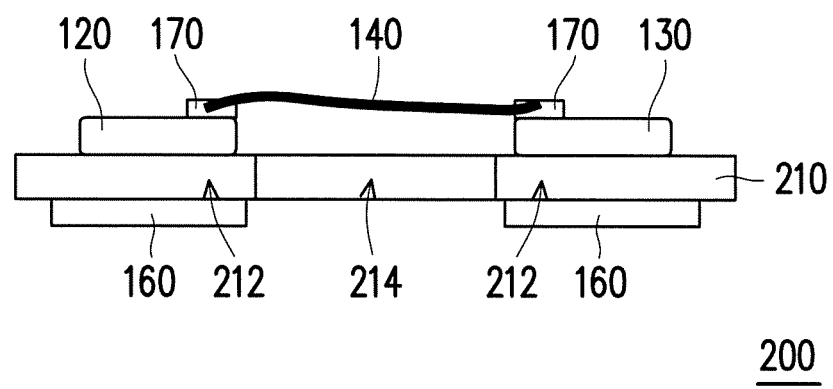
FIG. 5 is a side view schematic diagram of the second respiration sensing module according to another embodiment of the disclosure.

FIG. 5 is a side view schematic diagram of the second respiration sensing module according to another embodiment of the disclosure. Referring to FIG. 5, a second respiration sensing module 200 of the present embodiment is similar to the second respiration sensing module 100' of FIG. 4, and only the differences between the two are described here. The substrate 110 of FIG. 4 is entirely a stretchable substrate, while the substrate 210 of FIG. 5 has two non-stretchable regions 212 and a stretchable region 214 located between the two non-stretchable regions 212. The first electrode 120 and the second electrode 130 are respectively located at the two non-stretchable regions 212. Therefore, the first electrode 120 and the second electrode 130 can be preferably fixed onto the body of the user. The stretchable region 214 allows the distance between the first electrode 120 and the second electrode 130 to change with the respiration of the user.

Figure 6:
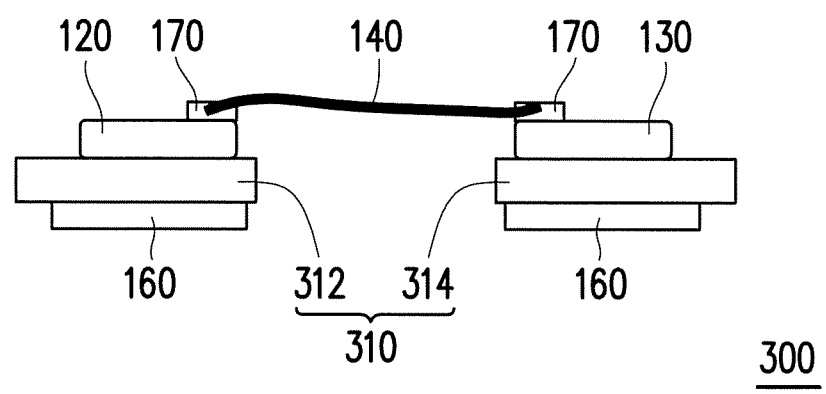
FIG. 6 is a side view schematic diagram of the second respiration sensing module according to another embodiment of the disclosure.

FIG. 6 is a side view schematic diagram of the second respiration sensing module according to yet another embodiment of the disclosure. Referring to FIG. 6, a second respiration sensing module 300 of the present embodiment is similar to the second respiration sensing module 100' of FIG. 4, and only the differences between the two are described here. A substrate 310 of the present embodiment includes a first portion 312 and a second portion 314 separated from each other. The first electrode 120 is located at the first portion 312, and the second electrode 130 is located at the second portion 314. As the first portion 312 is separate from the second portion 314, the distance between the first portion 312 and the second portion 314 may change with the respiration of the user, that is, the length of the stretchable conductive element 140 may change with the respiration of the user.

Figure 7:
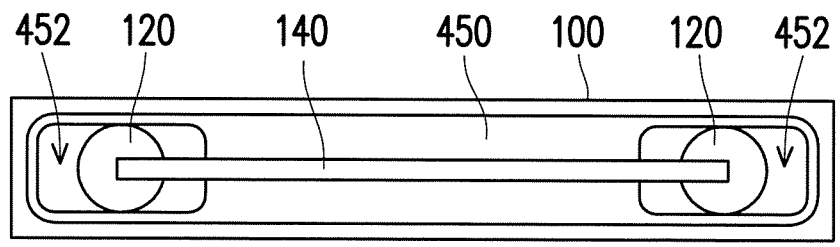
FIG. 7 is a top view schematic diagram of the second respiration sensing module according to yet another embodiment of the disclosure.

FIG. 7 is a top view schematic diagram of the second respiration sensing module according to yet another embodiment of the disclosure. Referring to FIG. 7, a second respiration sensing module 400 of the present embodiment is similar to the second respiration sensing module 100' of FIG. 4, and only the differences between the two are described here. A distance control member 450 of the second respiration sensing module 400 of the embodiment of the disclosure has two grooves 452, the first electrode 120 and the second electrode 130 are respectively located within the two grooves 452. The size of the distance control member 450 remains substantially fixed, that is, the distance between the two grooves 452 remains substantially fixed. Therefore, the distance between the first electrode 120 and the second electrode 130 may be limited and not excessively shortened, so as to control the length of the stretchable conductive element 140 to be greater than or equal to a preset value.

Figure 8:
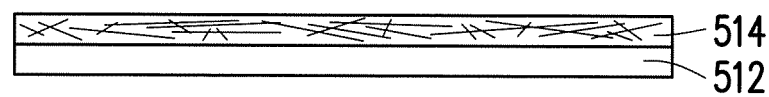
FIG. 8 is a schematic diagram of a stretchable conductive element of the second respiration sensing module according to an embodiment of the disclosure.

FIG. 8 is a schematic diagram of the stretchable conductive element of the second respiration sensing module according to the present embodiment. The stretchable conductive element 510 of the embodiment of the disclosure includes a base 512 and a conductive material 514 disposed on the base 512. The stretchable conductive element 510 of the present embodiment may be applied in each of the foregoing embodiments. For example, the base 512 may be thermoplastic polyurethane (TPU) or other suitable material, and the conductive material 514 may be silver or other suitable material. The conductive material 514, for example, is formed on the base 512 by deposition, printing or other modes. In order to improve the stretchability of the stretchable conductive element 510, the conductive material 514 may be formed to have a meandering shape, or the conductive material 514 may be formed in multiple layers, or the volume of the conductive material 514 may be increased.

Figure 9:
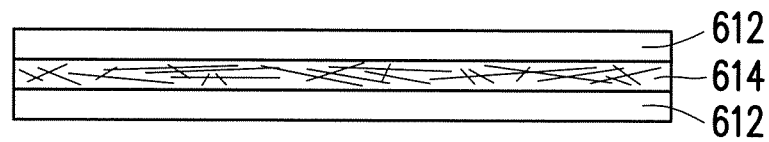
FIG. 9 is a schematic diagram of the stretchable conductive element of the second respiration sensing module according to another embodiment of the disclosure.

FIG. 9 is a schematic diagram of the stretchable conductive element of the second respiration sensing module according to another embodiment of the disclosure. Referring to FIG. 9, a conductive element 610 of the present embodiment is similar to the conductive element 510 of FIG. 8, and the difference is that the stretchable conductive element 610 of the present embodiment includes two layers of base 612 and a conductive material 614 disposed between the two layers of base 612. The stretchable conductive element 610 of the present embodiment may be applied in each of the foregoing embodiments. The resistance value of the stretchable conductive element 610 of the present embodiment changes relatively mildly, thus, having better stretchability so as to prevent the resistance from changing too drastically as the length changes.

Figure 10:
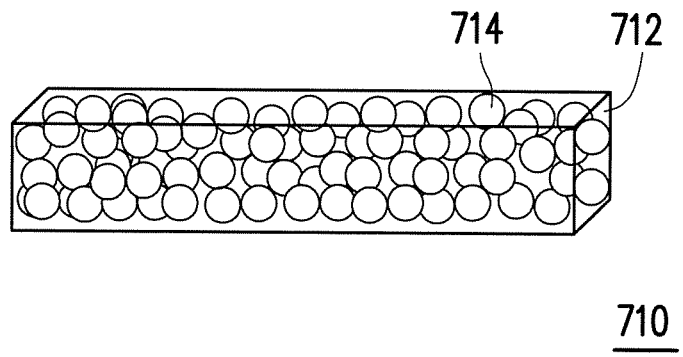
FIG. 10 and FIG. 11 are schematic diagrams of the stretchable conductive element of the second respiration sensing module according to another two embodiments of the disclosure.
Figure 11:
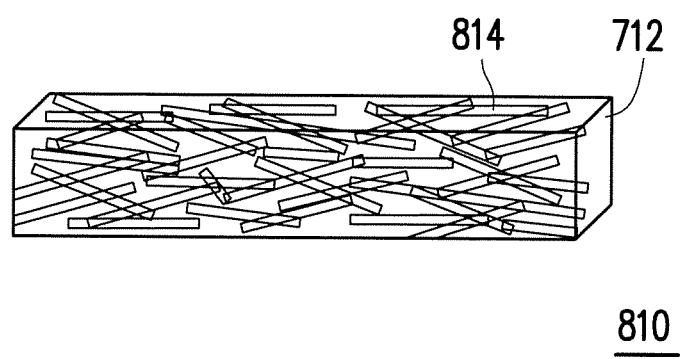

FIG. 10 and FIG. 11 are schematic diagrams of the stretchable conductive element of the second respiration sensing module according to another two embodiments of the disclosure. Referring to FIG. 10 and FIG. 11, a stretchable conductive element 710 and a stretchable conductive element 810 of the two embodiments are similar to each other, where both are composed of an insulating base 712 and conductive particles 714 and conductive particles 814 mixed in the insulating base 712, and the difference is that the conductive particles 714 are granular while the conductive particles 814 are in strips. Both the stretchable conductive element 710 and the stretchable conductive element 810 may be applied in each of the forgoing embodiments. In addition, the stretchable conductive element 710 and the stretchable conductive element 810 can also be used as a conductive material in the embodiments of FIG. 8 and FIG. 9. The material of the insulating base 712 includes an elastomer such as resin, rubber, silicone, or other suitable material. The material of the conductive material is, for example, metal nanoparticles, metal micro particles, metal nanowire, metal micro wire, carbon nanotube, graphite, carbon black, conductive polymer or other suitable material.

In summary of the above, regarding the wearable device of the embodiment of the disclosure, the respiration condition of the user is judged according to two types of respiration information, which can more accurately determine whether a critical situation will occur. The wearable device and respiration sensing module of the embodiment of the disclosure can prevent the possibility of being unable to determine a critical situation from happening by merely monitoring the heartbeat. In the respiration sensing module of the embodiment of the disclosure, the length of the stretchable conductive element can be controlled to be greater than or equal to a preset value, so as to reduce the noise interference. In addition, when the heartbeat of the user is additionally monitored, the additional monitoring of respiration may also further increase the success rate of judging the occurrence of a critical condition and can more accurately determine whether a critical situation will happen. Furthermore, the wearable device and the respiration sensing module of the embodiments of the disclosure also have the advantages of a simple structure and low cost, which are both helpful for improving the working efficiency of caregivers and integrated care of the elderly and children.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A wearable device comprising:
a first respiration sensor, configured to sense respiration of a user to obtain a first respiration information; and
a second respiration sensing module, configured to sense respiration of the user to obtain a second respiration information, wherein the second respiration sensing module comprises:
a substrate;
a first electrode, disposed on a first surface of the substrate;
a second electrode, disposed on the first surface of the substrate;
a stretchable conductive element, physically and electrically connected between the first electrode and the second electrode; and
a distance control member configured to control the length of the stretchable conductive element to be greater than or equal to a preset value,
wherein the respiration of the user is judged according to the first respiration information and the second respiration information, and a projection of the first electrode and the second electrode on the substrate does not overlap with a projection of the distance control member on the substrate.

2. The wearable device according to claim 1, wherein at least one of the first respiration information and the second respiration information comprises a respiratory rate.

3. The wearable device according to claim 1, wherein the stretchable conductive element comprises a base and a conductive material disposed on the base.

4. The wearable device according to claim 3, wherein the base is a thermoplastic polyurethane.

5. The wearable device according to claim 3, wherein the conductive material is silver.

6. The wearable device according to claim 1, wherein the material of the substrate comprises polyurethane or polysiloxane.

7. The wearable device according to claim 1, wherein the substrate has two non-stretchable regions and a stretchable region located between the non-stretchable regions, the first electrode and the second electrode are respectively located at the non-stretchable regions.

8. The wearable device according to claim 1, wherein the substrate comprises a first part and a second part separated from each other, the first electrode and the second electrode are respectively located at the first part and the second part.

9. The wearable device according to claim 1, wherein the first respiration sensor is an electrocardiogram (ECG) sensor, a gravity sensor or an ECG derived respiration (EDR) sensor.

10. The wearable device according to claim 1, wherein a distance between the first electrode and the second electrode is variable.

11. The wearable device according to claim 1, wherein the second respiration sensing module further comprises a plurality of patches, disposed on a second surface of the substrate opposite to the first surface and positioned correspondingly to the first electrode and the second electrode.

12. A respiration sensing module comprising:
a substrate;
a first electrode, disposed on a first surface of the substrate;
a second electrode, disposed on the first surface of the substrate;
a stretchable conductive element, physically and electrically connected between the first electrode and the second electrode; and
a distance control member for controlling the length of the stretchable conductive element to be greater than or equals to a preset value,
wherein a projection of the first electrode and the second electrode on the substrate does not overlap with a projection of the distance control member on the substrate.

13. The respiration sensing module according to claim 12, wherein the distance control member is a blocking wall or a groove, configured to limit the distance between the first electrode and the second electrode.

14. The respiration sensing module according to claim 12, wherein the stretchable conductive element comprises a base and a conductive material disposed on the base.

15. The respiration sensing module according to claim 14, wherein the base is a thermoplastic polyurethane.

16. The respiration sensing module according to claim 14, wherein the conductive material is silver.

17. The respiration sensing module according to claim 12, wherein the substrate is a stretchable substrate.

18. The respiration sensing module according to claim 17, wherein the material of the substrate comprises polyurethane or polysiloxane.

19. The respiration sensing module according to claim 12, wherein the substrate has two non-stretchable regions and a stretchable region located between the non-stretchable regions, the first electrode and the second electrode are respectively located at the non-stretchable regions.

20. The respiration sensing module according to claim 12, wherein the substrate comprises a first part and a second part separated from each other, the first electrode and the second electrode are respectively located at the first part and the second part.

21. The respiration sensing module according to claim 12, wherein a distance between the first electrode and the second electrode is variable.

22. The respiration sensing module according to claim 12, further comprises a plurality of patches disposed on a second surface of the substrate opposite to the first surface and positioned correspondingly to the first electrode and the second electrode.

* * * * *